(12) United States Patent
Kim et al.

(10) Patent No.: US 8,237,784 B2
(45) Date of Patent: Aug. 7, 2012

(54) METHOD OF FORMING VIRTUAL ENDOSCOPE IMAGE OF UTERUS

(75) Inventors: Sung Hee Kim, Seoul (KR); Sung Yoon Kim, Seoul (KR)

(73) Assignee: Medison Co., Ltd., Kangwon-Do (KR)

( * ) Notice: Subject to any disclaimer, the term of this patent is extended or adjusted under 35 U.S.C. 154(b) by 414 days.

(21) Appl. No.: 12/608,721

(22) Filed: Oct. 29, 2009

(65) Prior Publication Data

US 2010/0118124 A1    May 13, 2010

(30) Foreign Application Priority Data

Nov. 10, 2008  (KR) .......................... 10-2008-0110969
Oct. 9, 2009   (KR) .......................... 10-2009-0096159

(51) Int. Cl.
*H04N 9/47* (2006.01)
(52) U.S. Cl. .......................................... 348/77; 348/65
(58) Field of Classification Search .................. None
See application file for complete search history.

(56) References Cited

U.S. PATENT DOCUMENTS

| | | | |
|---|---|---|---|
| 6,369,812 B1 | 4/2002 | Iyriboz et al. | |
| 6,606,091 B2 * | 8/2003 | Liang et al. | 345/424 |
| 8,021,300 B2 * | 9/2011 | Ma et al. | 600/437 |
| 8,079,957 B2 * | 12/2011 | Ma et al. | 600/438 |
| 2005/0171419 A1 * | 8/2005 | De Ziegler | 600/407 |

FOREIGN PATENT DOCUMENTS

JP    11-313816    11/1999

OTHER PUBLICATIONS

Korean Office Action issued in Korean Patent Application No. 10-2009-0096159, mailed Jan. 11, 2011.
Yuh, E., et al., "Virtual Endoscopy Using Perspective Volume-Rendered Three-Dimensional Sonographic Data: Technique and Clinical Applications", Computers in Radiology, May 1999, pp. 1193-1197, vol. 172, American Roentgen Ray Society.

* cited by examiner

*Primary Examiner* — John B. Walsh
(74) *Attorney, Agent, or Firm* — McDermott Will & Emery LLP

(57) ABSTRACT

A method of forming a virtual endoscope image of a uterus is disclosed. The virtual image showing an inner wall of a uterus is formed from a three-dimensional ultrasound uterus image obtained by hysterosalpingography with a solution. An inner wall of the uterus in the 3D virtual image is inspected and a virtual endoscope image of the uterus is formed by reflecting the inspection result on the 3D virtual uterus image. Also, the virtual endoscope images in every aspect are provided according to the positions of a view point or virtual light source. Thus, the inner wall of the uterus can be inspected more easily.

18 Claims, 9 Drawing Sheets

VEI 1

VEI 2

VEI 3

VEI 4

VEI 5

VEI 6

VEI 7

METHOD OF FORMING VIRTUAL ENDOSCOPE IMAGE OF UTERUS

The present application claims priority from Korean Patent Application Nos. 10-2008-0110969 filed on Nov. 10, 2008, and 10-2009-0096159 filed on Oct. 9, 2009, the entire subject matter of which is incorporated herein by reference.

TECHNICAL FIELD

The present disclosure generally relates to an ultrasound diagnosis, and more particularly to a method of forming a virtual endoscope image of a uterus using a three-dimensional (3D) ultrasound image of the uterus.

BACKGROUND

An ultrasound system has been widely used for examining a woman's uterus. For example, the ultrasound system is utilized in cervical examinations, hysterosalpingography (HSG) and 3D HSG with a saline solution. With the cervical examination that is invasive, it is difficult to investigate the patency of the cervix and an external shape of the uterus. Moreover, the cervical examination may cause perforation, infection or bleeding in the uterus. In case of the HSG there are many problems of causing a pain, using a contrast medium and exposure to radiation. The 3D HSG with the saline solution can be performed non-invasively, and thus, the patients show little rejection. However, the quality of the image obtained by the 3D HSG with the saline solution is degraded in comparison with the images obtained by the cervical examination or the HSG. Thus, it is difficult to discriminate between an inner wall and an inner portion of the uterus, as well as to find lesion with the unaided eye.

SUMMARY

Embodiments for forming a virtual endoscope image of a uterus are disclosed herein. In one embodiment, by way of non-limiting example, a method of forming a virtual endoscope image of a uterus with an ultrasound system, comprises: extracting pixel information of a boundary between an inner portion and an outer portion of the uterus on two-dimensional (2D) uterus images by a processor within the ultrasound system; removing the inner portion of the uterus on each 2D uterus image based on the pixel information of the boundary and forming 2D images of a uterus shell by the processor within the ultrasound system, wherein the uterus shell includes an inner wall and an outer wall; forming a 3D virtual image of the uterus shell with the 2D images of the uterus shell by the processor within the ultrasound system; inspecting the inner wall of the uterus in the 3D virtual image by the processor within the ultrasound system; and forming a virtual endoscope image of the uterus by reflecting the inspection result on the 3D virtual uterus image by the processor within the ultrasound system.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
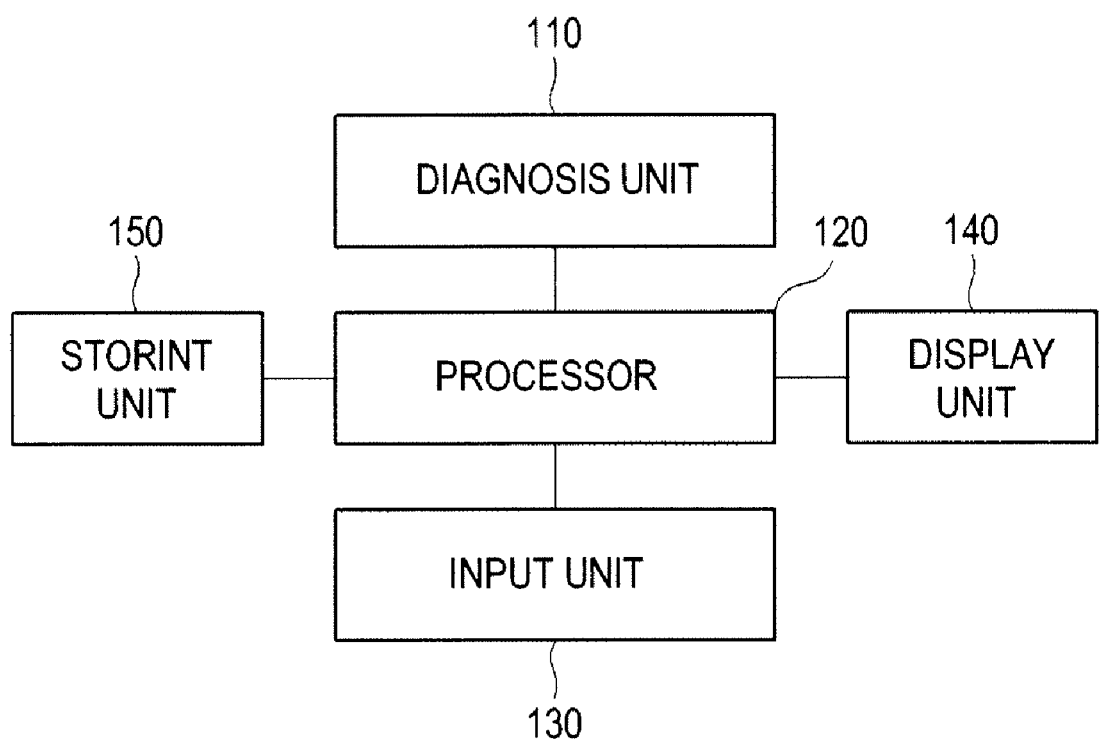
FIG. 1 is a block diagram showing an illustrative embodiment of an ultrasound system.

FIG. 1 is a block diagram showing an illustrative embodiment of an ultrasound system 100 including a diagnosis unit 110, a processor 120, an input unit 130, a display unit 140 and a storing unit 150. The diagnosis unit 110 may provide a three-dimensional (3D) uterus ultrasound image data in real time. The diagnosis unit 110 may include a probe (not shown), a beam former (not shown), etc. The 3D uterus image may be obtained by 3D hysterosalpingography (HSG) with a saline solution, which is injected into the uterus at the body temperature for expanding the uterine cavity. The saline solution may be replaced with a Ringer's solution and a glycine solution. A vaginal probe may be used to obtain the 3D ultrasound image of the uterus. The 3D uterus ultrasound image data formed by the diagnosis unit 110 may be stored in the storing unit 150. The storing unit 150 may provide the 3D uterus ultrasound image data in response to a user's request such as the request of displaying the 3D uterus ultrasound image or forming a virtual endoscope image of the uterus.

Figure 2:
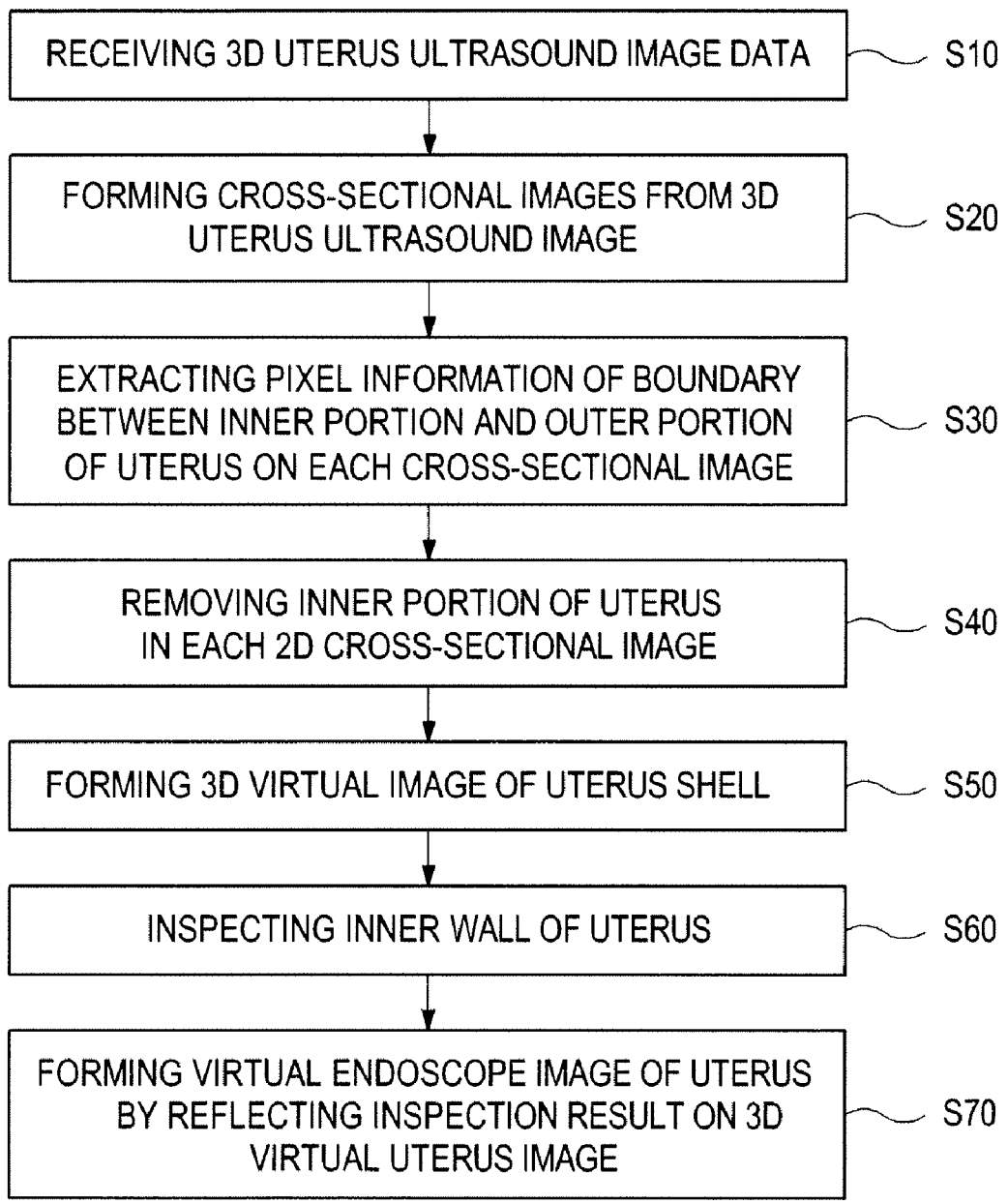
FIG. 2 is a block diagram showing an illustrative embodiment of a process of forming a virtual endoscope image of a uterus using the ultrasound system shown in FIG. 1.
Figure 3:
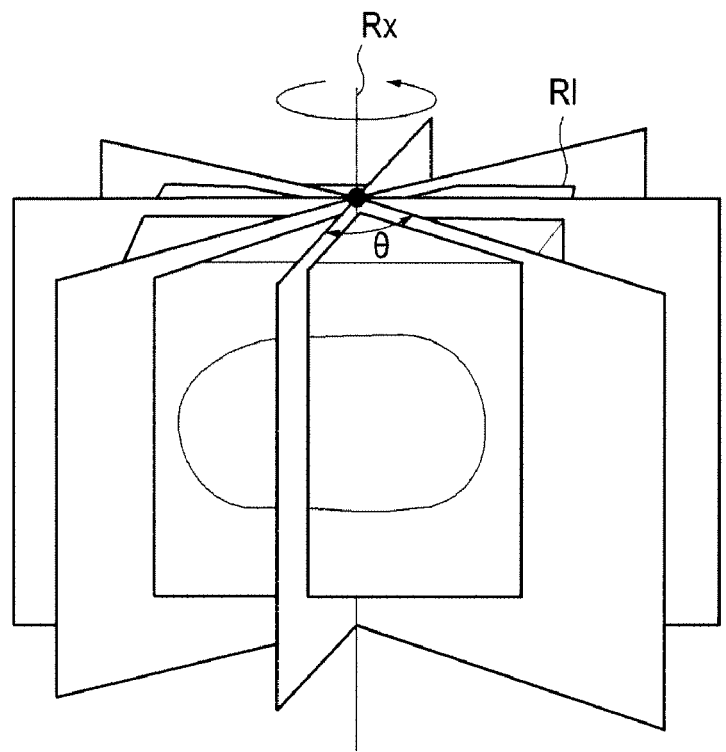
FIG. 3 is a schematic diagram showing a three-dimensional (3D) uterus ultrasound image.
Figure 4:
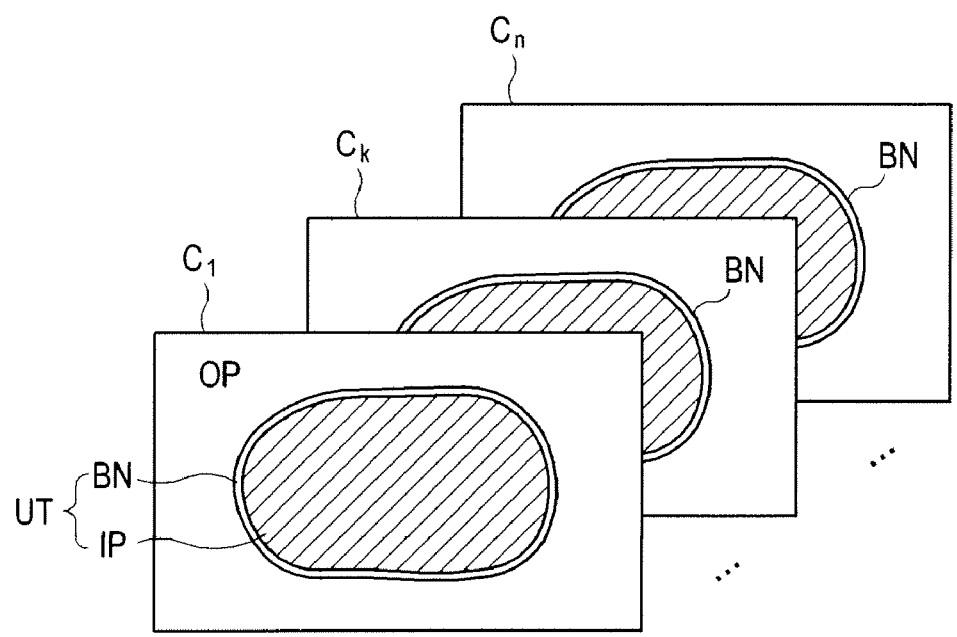
FIG. 4 shows schematic diagrams of cross-sectional images formed with the 3D uterus ultrasound images.

The processor 120 of the ultrasound system 100 may form a virtual endoscope image of the uterus by using the 3D uterus image data of the uterus. Referring to FIG. 2, the processor 120 may receive the 3D uterus ultrasound image data from the 3D ultrasound uterus image data providing unit, i.e., from the diagnosis unit 110 or the storing unit 150 (S10). As shown in FIG. 3, the processor 120 may set a virtual rotational axis Rx passing through a 3D uterus ultrasound image RI. The processor 120 may form a plurality of cross-sectional images $C_1$ to $C_n$ by rotating the 3D uterus image RI by specified angles θ around the rotation axis Rx, as shown in FIG. 4 (S20). Pixel information of a boundary BN between an inner portion IP and outer portion OP of the uterus UT on each cross-sectional image $C_1$ to $C_n$ may be extracted by the processor 120 (S30). The boundary BN may be the endometrium.

To extract the pixel information of the boundary BN, the processor 120 may perform boundary extraction on each of the cross-sectional images $C_1$ to $C_n$. The extraction of pixel information of the boundary BN may be performed either automatically or manually. In the case of the automatic extraction, the processor 120 may perform an adaptive binarization process, a morphological filtering and a region growing on the cross-sectional images $C_1$ to $C_n$ one after another. Thus, the processor 120 may extract the pixel information of the boundary BN between inner portion IP and outer portion OP of the uterus UT. For the manual extraction, the cross-sectional images $C_1$ to $C_n$ may be displayed on the display device 140. A user may designate the boundary BN between the inner portion IP and the outer portion OP of the uterus UT on each of the cross-sectional images $C_1$ to $C_n$ through the input unit 130. The processor 120 may extract the pixel information of the boundary BN on each of the cross-sectional images $C_1$ to $C_n$ with the designated boundary.

Figure 5:
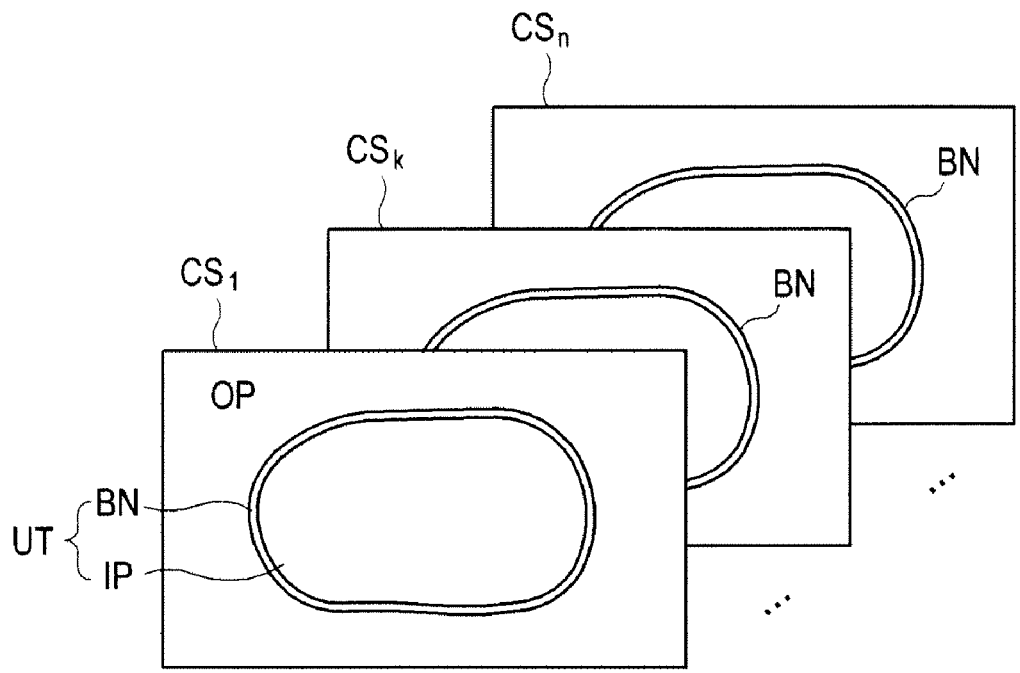
FIG. 5 shows an illustrative embodiment of cross-sectional shell images formed with the cross-sectional images shown in FIG. 4.
Figure 6:
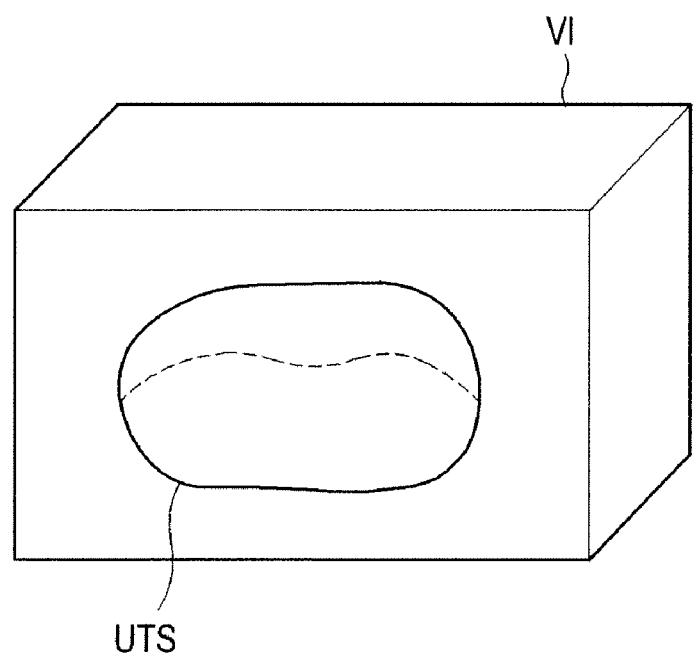
FIG. 6 is a schematic diagram of a 3D virtual image of the uterus shell formed with the cross-sectional shell images shown in FIG. 5.

The processor 120 may remove inner portion IP of the uterus UT in each cross-sectional image $C_1$ to $C_n$ based on the extracted pixel information of the boundary BN (S40) to form cross-sectional shell images $CS_1$ to $CS_n$, as shown in FIG. 5. Referring to FIG. 6, the processor 120 may form a 3D virtual image VI of uterus shell UTS with the cross-sectional shell images $CS_1$ to $CS_n$ based on the extracted pixel information of the boundary BN (S50). To form the 3D virtual image VI, the processor 120 may perform an interpolation process to form an appropriate number of interpolated images (not shown) between every adjacent two cross-sectional shell images $CS_1$ and $CS_2$, $CS_2$ and $CS_3$ ... $CS_{n-1}$ and $CS_n$ and form the 3D virtual image VI of the uterus shell UTS by performing a surface-rendering process with the cross-sectional shell images $CS_1$ to $CS_n$ and the interpolated images.

Figure 7:
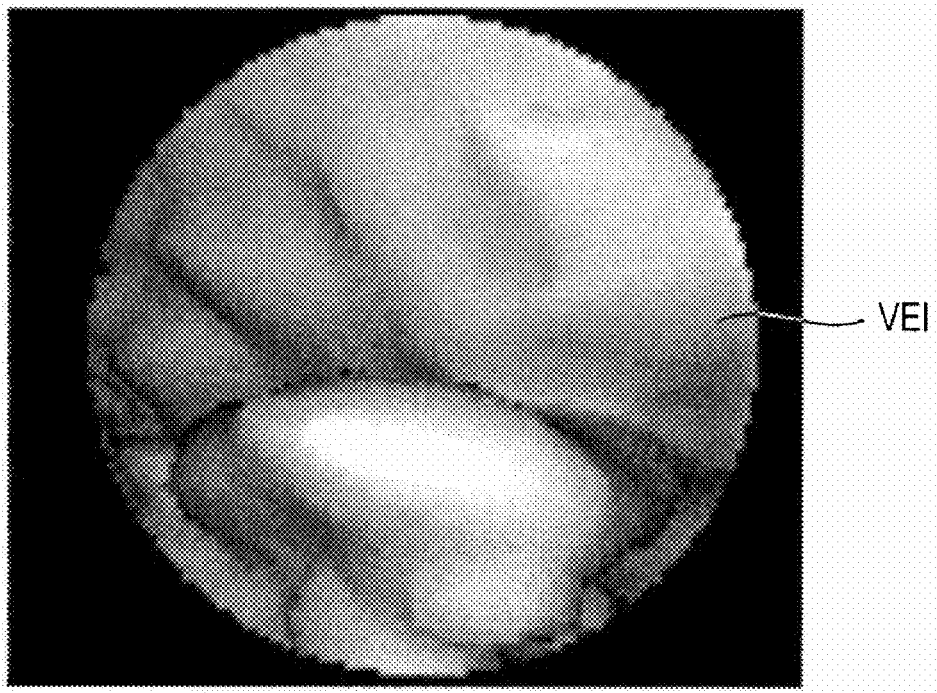
FIG. 7 is a picture of a virtual endoscope image showing a part of an inner wall of the uterus.

The processor 120 may inspect whether any abnormal part exists by automatically detecting brightness variance of voxels and curvature variance on an inner wall of the uterus (S60). An inspection result obtained by the inspection may include position information of the abnormal part if the abnormal part has been found or a particular part of the inner wall of the uterus if any abnormal parts have not been found. For instance, uterine polyps are shown as hyperechoic regions in a 3D ultrasound image while submucosal fibroids are shown as hypoechoic regions. Thus, the abnormal parts such as the uterine polyps or submucosal fibroids can be found by comparing brightness value of voxels of the inner wall. The endometrial cancer and tumor are shown as swollen regions in the 3D ultrasound image. Thus, endometrial cancer and tumor can be found by detecting regions where the curvature is excessively varied than a predetermined value. The processor 120 may form a virtual endoscope image of the uterus by reflecting the inspection result on the 3D virtual uterus image (S70). FIG. 7 shows a virtual endoscope image VEI showing a part of the inner wall of the uterus.

Figure 8:
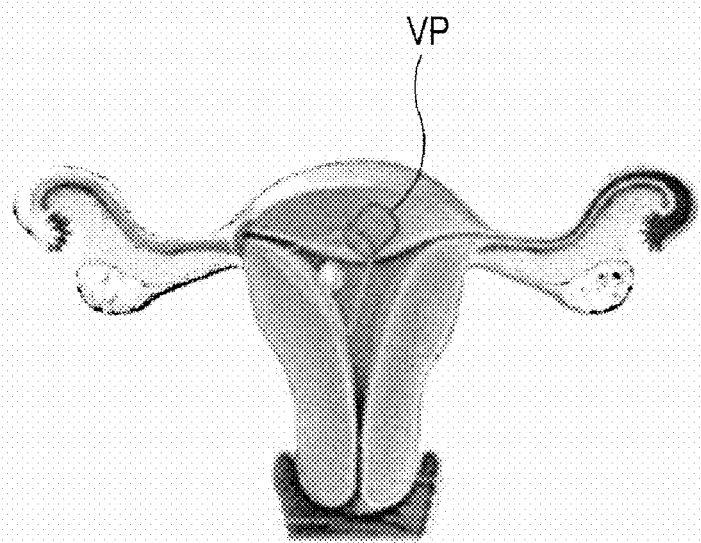
FIG. 8 is a schematic diagram of a guide image showing a schematic structure of the uterus and a view point.

The processor 120 may form a guide image VP_IMG, as shown in FIG. 8, based on the extracted pixel information of the boundary between the inner portion and outer portion of the uterus with the inspection result. The view point VP may be an inspection position facing the part of the inner wall of the uterus shown in the virtual endoscope image VEI. In response to a view point display request through the input unit 130 or at the time of displaying the virtual endoscope image VEI, the processor 120 may form the guide image VP_IMG with the view point VP arranged to be faced with the part of the inner wall having been shown in the virtual endoscope image VEI. The guide image VP_IMG may be displayed with the virtual endoscope image VEI on the display unit 140. The user may change the position of the view point VP on the guide image VP_IMG with the input unit 130 like a track ball, a mouse or a keyboard. In response to receipt of new position of the view point VP from the user, the processor 120 may form a new virtual endoscope image based on the moved position of the view point VP and display the new virtual endoscope image on the display unit 140. Thus, the new virtual endoscope image can show another part of the inner wall facing the moved view point VP.

Figure 9:
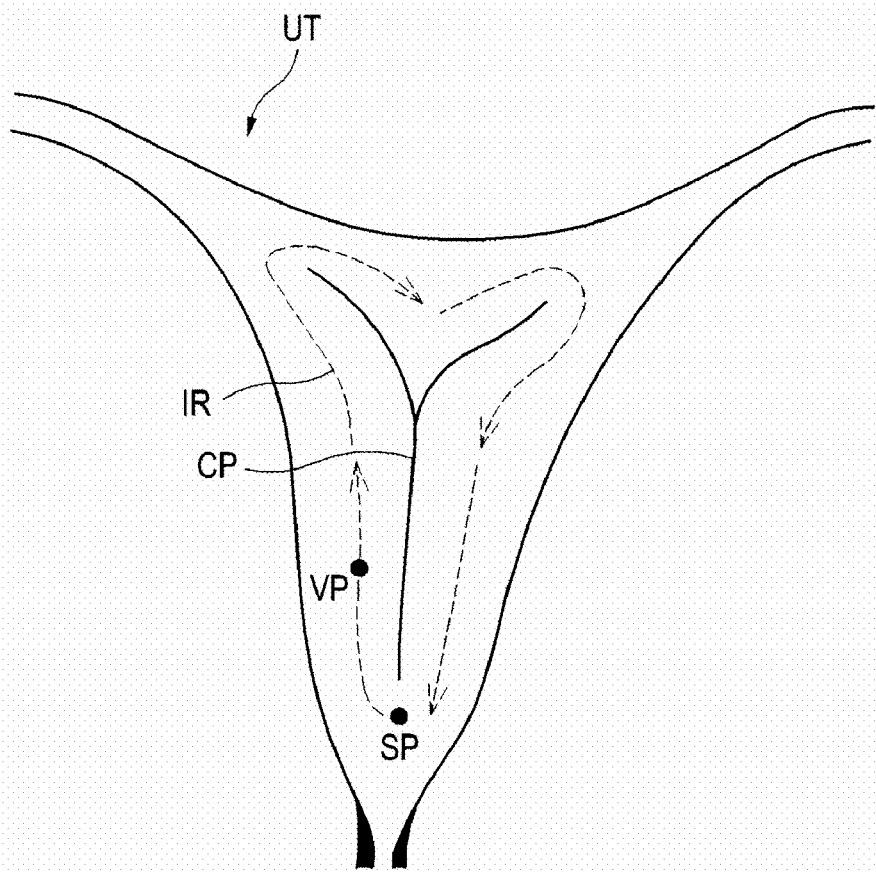
FIG. 9 is a schematic diagram of an inspection guide image.

In accordance with another embodiment, the processor 120 may form an inspection guide image (navigation image) showing a schematic structure of the uterus and the view point VP based on the extracted pixel information of the boundary BN in response to an inspection guide image display request through the input unit 130 or at the time of displaying the virtual endoscope image VEI. In the embodiment, the processor 120 may set a central path CP and an inspection route IR on the guide image based on the extracted pixel information of the boundary BN between the inner portion and outer portion of the uterus, as shown in FIG. 9. The inspection rout IR may be set with points having constant distances from the central path CP. At the beginning, the view point VP may be positioned at a starting point and move along the inspection route IR at a preset speed. When the view point VP moves along the inspection route IR, the processor 120 may change the virtual endoscope image VEI based on the position of the view point VP. That is, the parts of the inner wall of the uterus having been shown in the virtual endoscope image VEI can be changed to face the moving view point VP.

Figure 10A:
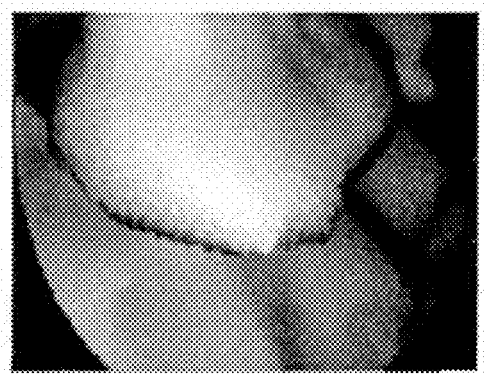
FIGS. 10A to 10C are pictures of reconstructed endoscope images with three different spot sizes of a virtual light source.
Figure 10B:
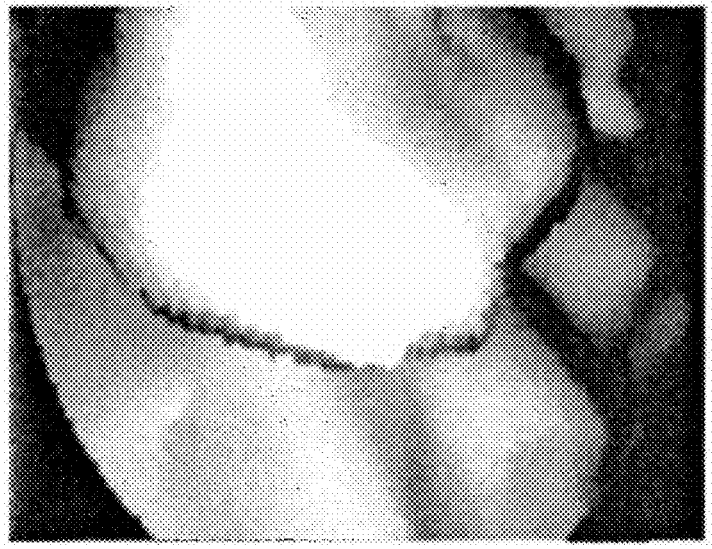
Figure 10C:
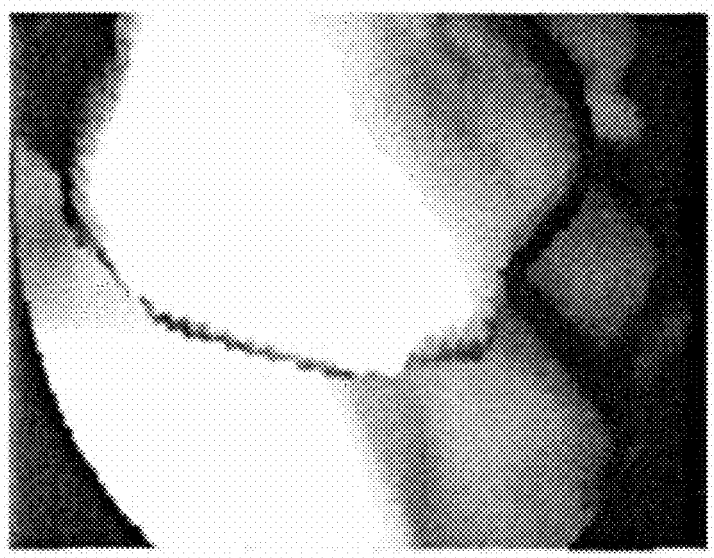
Figure 11A:
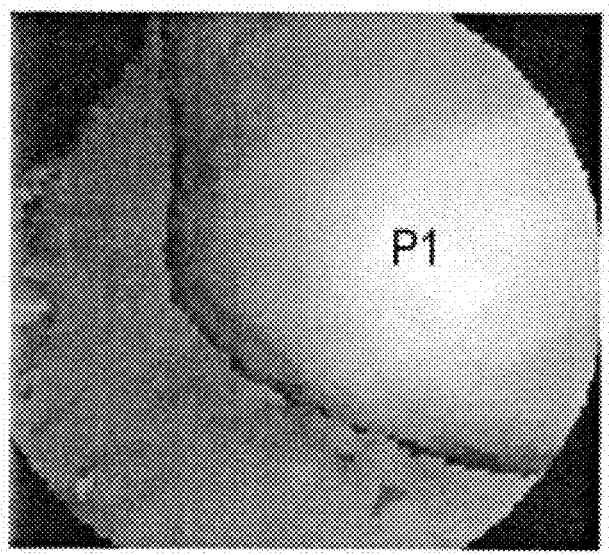
FIGS. 11A to 11D are pictures of reconstructed endoscope images with four different positions P1 to P4 of the virtual light source.
Figure 11B:
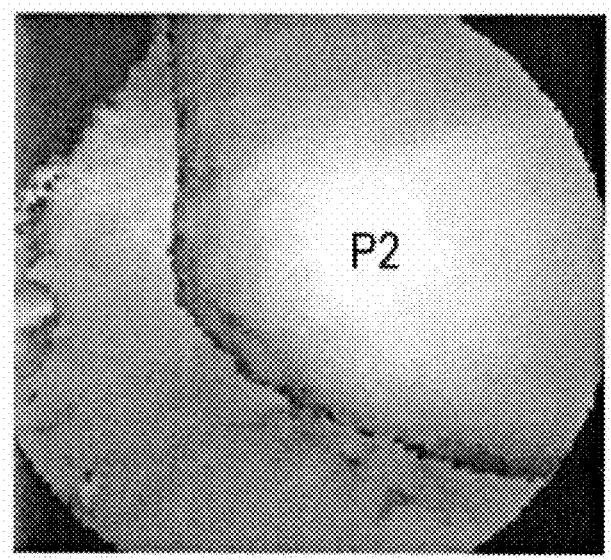
Figure 11C:
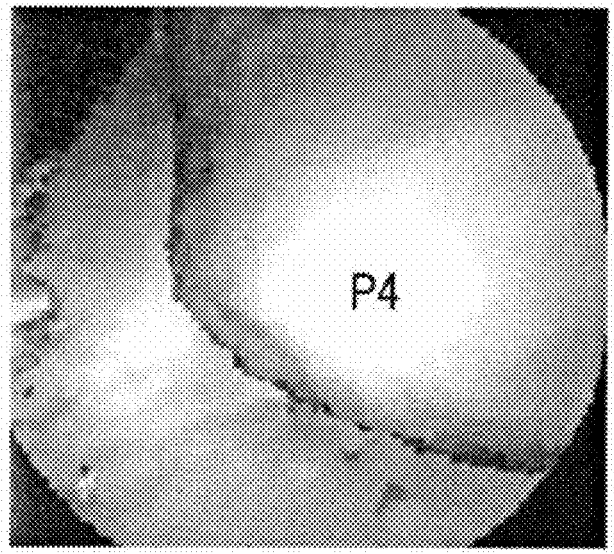
Figure 11D:
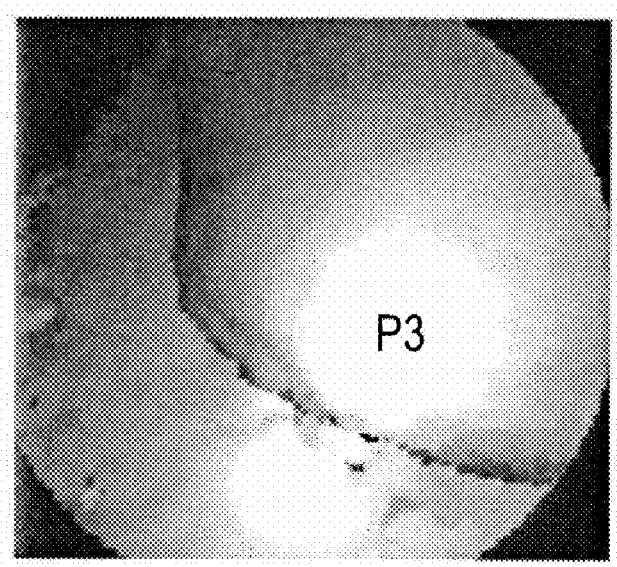

While the view point VP moves, small size tumors may not be detected. Thus, the user may fix the view point on a suspicious region where a tumor is expected to exist according to a hold instruction inputted through the input unit 130. On the suspicious region, the processor 120 may form a plurality of new endoscope images by reconstructing the virtual endoscope image with different spot sizes or positions of a virtual light source. Thus, the plurality of the new endoscope images can show shadow changes according to the spot sizes or the positions of the virtual light source. FIGS. 10A to 10C show reconstructed endoscope images VEI1 to VEI3 with three different spot sizes of the virtual light source. FIGS. 11A to 11D show reconstructed endoscope images at four different positions P1 to P4 of the virtual light source. With reconstructed endoscope image VEI4 to VEI 7 formed by reflecting the spot size or the positions of the virtual light source, tumors can be detected more easily.

In accordance with another embodiment of the present invention, there is provided a computer readable medium comprising instructions for performing the method of forming a virtual endoscope image of a uterus. The medium may include magnetic hard or floppy disks drives, optical drives or CD-ROMs, and any memory technology based on semiconductors or other materials, whether implemented as read-only or random access memory.

As described above, in accordance with embodiments, a virtual endoscope image showing an inner wall of a uterus may be formed automatically from a 3D ultrasound uterus image obtained by the 3D HSG with the saline solution. Automatic inspection may be performed to find abnormal parts on the inner wall of the uterus. Further, a virtual endoscope image of the uterus may be formed based on the inspection result. In accordance with another embodiment, it is possible to provide the virtual endoscope image in every aspect according to the positions of a view point or virtual light source. With the virtual endoscope image, a user can observe the inner wall of the uterus at a glance. Further, it is possible to minimize errors cause by the user's operation to detect the abnormal parts.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method of forming a virtual endoscope image of a uterus with an ultrasound system, comprising:
   extracting pixel information of a boundary between an inner portion and an outer portion of the uterus on two-dimensional (2D) uterus images by a processor within the ultrasound system;
   removing the inner portion of the uterus on said each 2D uterus image based on the pixel information of the boundary to form 2D images of a uterus shell by the processor within the ultrasound system, wherein the uterus shell includes an inner wall and an outer wall;
   forming a 3D virtual image of the uterus shell with the 2D images of the uterus shell by the processor within the ultrasound system; inspecting the inner wall of the uterus in the 3D virtual image by the processor within the ultrasound system; and
   forming a virtual endoscope image of the uterus by reflecting the inspection result on the 3D virtual uterus image by the processor within the ultrasound system.

2. The method of claim 1, before the step of extracting the pixel information of the boundary, further comprising:
   receiving a three-dimensional (3D) uterus ultrasound image data by a diagnosis unit within the ultrasound system; and
   forming the 2D uterus images from the 3D uterus ultrasound image by the processor within the ultrasound system.

3. The method of claim 2, wherein the 3D uterus ultrasound image data is obtained by 3D hysterosalpingography with a solution including saline, Ringer's solution and glycine solution, with the diagnosis unit of the ultrasound system.

4. The method of claim 2, wherein the step of extracting the pixel information of the boundary includes:
   receiving a boundary designating information to the boundary between the inner portion and outer portion of the uterus on said each 2D uterus image through an input unit within the ultrasound system; and
   extracting the pixel information of the boundary between the inner portion and outer portion of the uterus on said each 2D uterus image based on the boundary designating information by the processor within the ultrasound system.

5. The method of claim 2, wherein the step of inspecting the inner wall of the uterus includes detecting brightness variance of voxels and curvature variance on the inner wall of the uterus in the 3D virtual image.

6. The method of claim 2, wherein the virtual endoscope image of the uterus shows a part of the inner wall of the uterus shell, and
   after the step of forming the virtual endoscope image, further comprising steps of:
   forming a guide image showing a schematic structure of the uterus and a view point by the processor within the ultrasound system, wherein the view point faces with the part of the inner wall of the uterus; and
   displaying the guide image with the virtual endoscope image on a display unit within the ultrasound system.

7. The method of claim 6, after the step of displaying the guide image with the virtual endoscope image, further comprising steps of:
   receiving a new position of the view point through an input unit within the ultrasound system;
   forming a new virtual endoscope image showing another part of the inner wall of the uterus based on the new position of the view point by the processor within the ultrasound system; and
   displaying the new virtual endoscope image with the guide image having the view point at the new position on the display unit within the ultrasound system.

8. The method of claim 2, after the step of forming the virtual endoscope image further comprising steps of:
   forming an inspection guide image showing schematic structure of the uterus and a view point by the processor of the ultrasound system;
   setting a central path and an inspection route on the inspection guide image based on the extraction pixel information of the boundary between inner portion and the outer portion of the uterus by the processor within the ultrasound system;
   moving the view point along the inspection route by the processor within the ultrasound system; and
   changing the virtual endoscope image based on the moved position of the view point by the processor of the ultrasound system.

9. The method of claim 8, wherein the step of changing the endoscope image includes forming a plurality of new endoscope images by reconstructing the endoscope images showing shadow changes according to spot sizes or positions of a virtual light source.

10. A non-transitory computer readable medium comprising instructions which, when executed by a processor performs a method of forming a virtual endoscope image of a uterus, wherein the methods comprises steps of:
   extracting pixel information of a boundary between an inner portion and an outer portion of the uterus on two-dimensional (2D) uterus images;
   removing the inner portion of the uterus on said each 2D uterus images image based on the pixel information of the boundary to form 2D images of a uterus shell, wherein the uterus shell includes an inner wall and an outer wall;
   forming a 3D virtual image of the uterus shell with the 2D images of the uterus shell;
   inspecting the inner wall of the uterus in the 3D virtual image; and
   forming a virtual endoscope image of the uterus by reflecting the inspection result on the 3D virtual uterus image.

11. The medium of claim 10, before the step of extracting the pixel information of the boundary, the method further comprises:
   obtaining a three-dimensional (3D) uterus ultrasound image data; and
   forming the 2D uterus images from the 3D uterus ultrasound image.

12. The medium of claim 11, wherein the 3D uterus ultrasound image data is obtained by 3D hysterosalpingography with a solution including saline, Ringer's solution and glycine solution.

13. The medium of claim 11, wherein the step of extracting the pixel information of the boundary includes:

receiving a boundary designating information to the boundary between the inner portion and outer portion of the uterus on said each 2D uterus image; and extracting the pixel information of the boundary between the inner portion and outer portion of the uterus on said each 2D uterus image based on the boundary designating information.

14. The medium of claim 11, wherein the step of inspecting the inner wall of the uterus includes detecting brightness variance of voxels and curvature variance on the inner wall of the uterus in the 3D virtual image.

15. The medium of claim 11, wherein the virtual endoscope image of the uterus shows a part of the inner wall of the uterus shell, and after the step of forming the virtual endoscope image, the method further comprises steps of:

forming a guide image showing a schematic structure of the uterus and a view point, wherein the view point faces the part of the inner wall of the uterus; and displaying the guide image with the virtual endoscope image.

16. The medium of claim 15, after the step of displaying the guide image with the virtual endoscope image, the method further comprises steps of:

receiving a new position of the view point; forming a new virtual endoscope image showing another part of the inner wall of the uterus based on the new position of the view point; and displaying the new virtual endoscope image with the guide image having the view point at the new position.

17. The medium of claim 11, after the step of forming the virtual endoscope image, the method further comprises steps of:

forming an inspection guide image showing schematic structure of the uterus and a view point;

setting a central path and an inspection route on the inspection guide image based on the extraction pixel information of the boundary between inner portion and the outer portion of the uterus;

moving the view point along the inspection route; and changing the virtual endoscope image based on the moved position of the view point.

18. The medium of claim 17, wherein the step of changing the endoscope image includes forming a plurality of new endoscope images by reconstructing the endoscope images showing shadow changes according to spot sizes or positions of a virtual light source.

\* \* \* \* \*